United States Patent [19]

Knodle et al.

[11] Patent Number: 5,251,121
[45] Date of Patent: Oct. 5, 1993

[54] POWER SUPPLIES

[75] Inventors: Daniel W. Knodle, Seattle; Walter A. Cooke, Monroe; Paul K. Graham, Renton, all of Wash.

[73] Assignee: NTC Technology, Inc., Wilmington, Del.

[21] Appl. No.: 599,888

[22] Filed: Oct. 18, 1990

Related U.S. Application Data

[63] Continuation-in-part of Ser. No. 528,059, May 23, 1990, which is a continuation-in-part of Ser. No. 598,984, Oct. 17, 1990.

[51] Int. Cl.$^5$ .................................. H02M 7/537
[52] U.S. Cl. ........................... 363/98; 363/132; 363/58; 361/90; 361/111; 307/106
[58] Field of Search .................... 363/55–58, 363/95–98, 131, 132; 361/18, 90, 91, 111; 307/106

[56] References Cited

U.S. PATENT DOCUMENTS

| | | |
|---|---|---|
| 3,793,525 | 2/1974 | Burch et al. |
| 3,811,776 | 5/1974 | Blau, Jr. |
| 3,987,303 | 10/1976 | Stoft et al. |
| 4,011,859 | 3/1977 | Frankenberger |
| 4,107,771 | 8/1978 | Anderson et al. ............ 363/58 |
| 4,204,768 | 5/1980 | N'Guyen |
| 4,213,103 | 7/1980 | Birt ........................ 363/56 X |
| 4,268,751 | 5/1981 | Fritzlen et al. |
| 4,270,164 | 5/1981 | Wyman et al. ............... 363/56 |
| 4,371,785 | 2/1983 | Pederson |

OTHER PUBLICATIONS

Reliable, Accurate CO$_2$ Analyzer for Medical Use, Sloman, Hewlett Packard Journal, Sep. 1981, pp. 3–21.

*Primary Examiner*—Emanuel T. Voeltz
*Attorney, Agent, or Firm*—Hughes & Multer

[57] ABSTRACT

Power supplies for generating a stream of electrical pulses in which successive pulses have opposite polarities. The pulses are formed and outputted from pulse generating circuitry which has two complementary pairs of MOSFETs arranged in an H-bridge configuration. Other major components of the power supply are voltage regulators for supplying positive and negative operating pulses with selected, precisely controlled voltages to the driver and watchdog circuits for disenabling the pulse outputting circuitry if: the frequency of the operating pulses deviate from a selected range, the widths of the operating pulses exceed a selected maximum, extraneous pulses are present, or the voltage of the operating pulses falls below or exceeds selected maximums. In one important application, the power supply is employed to drive the emitter of an infrared radiation source.

18 Claims, 12 Drawing Sheets

PW WATCHDOG

FREQUENCY WATCHDOG

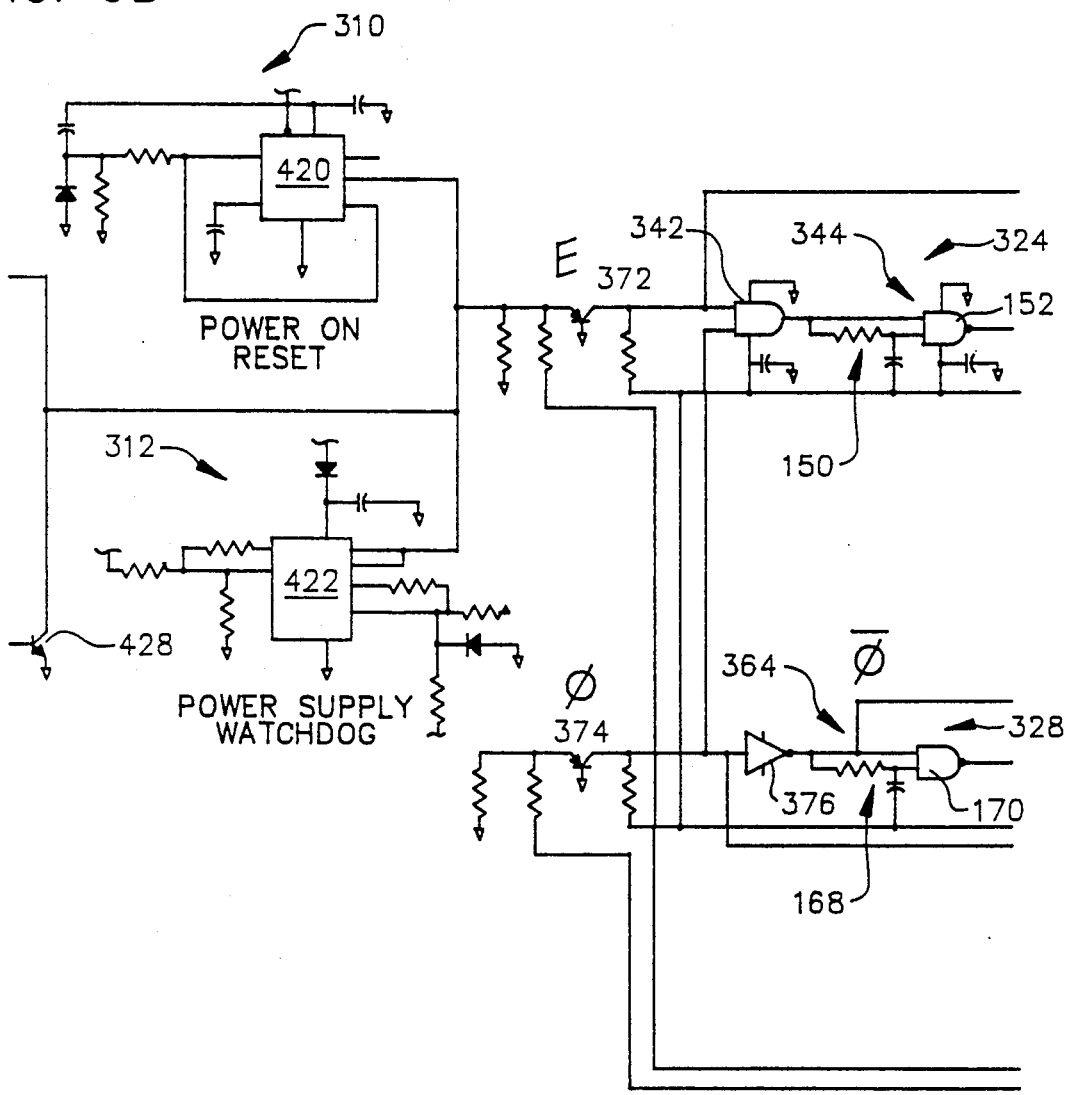

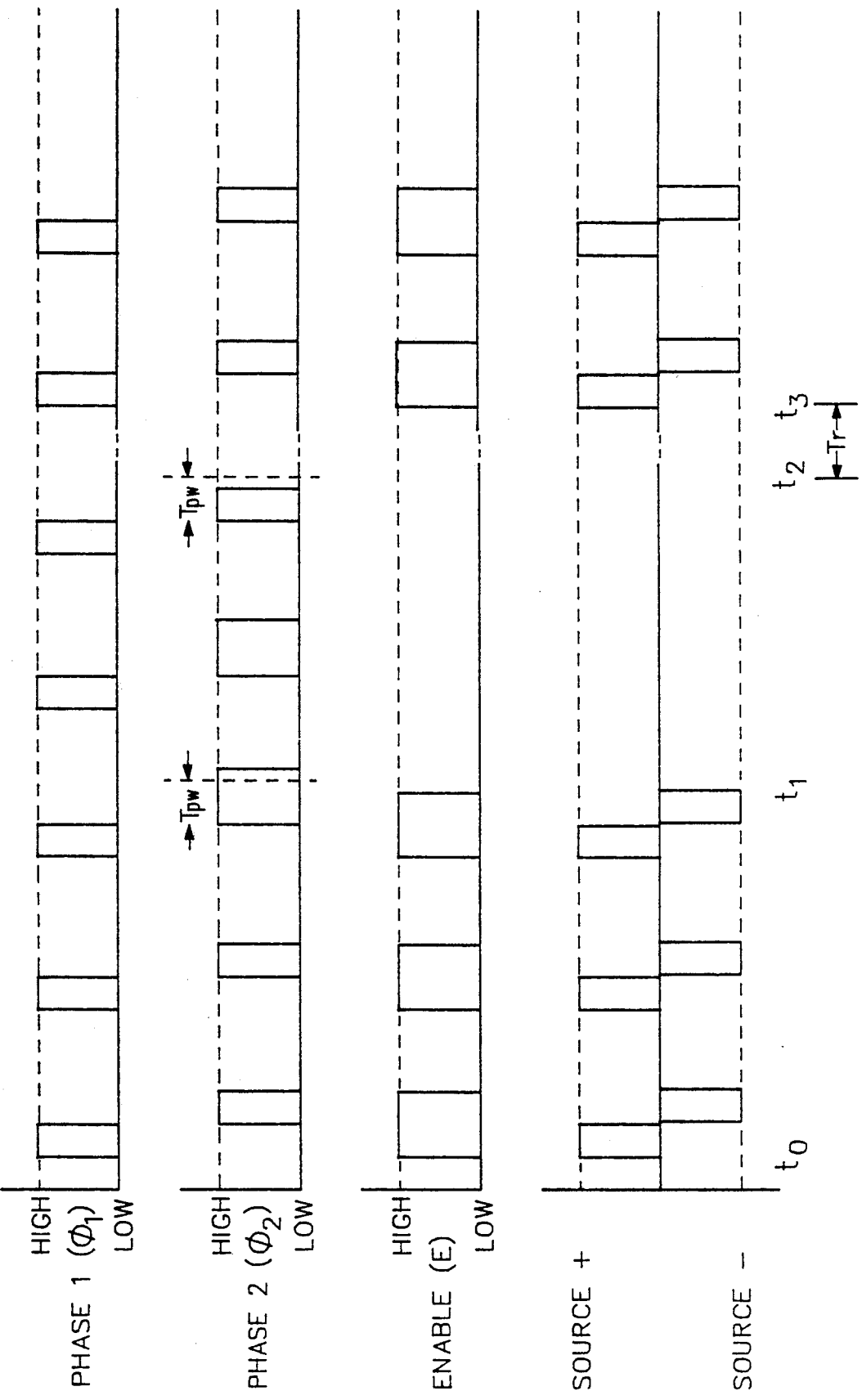

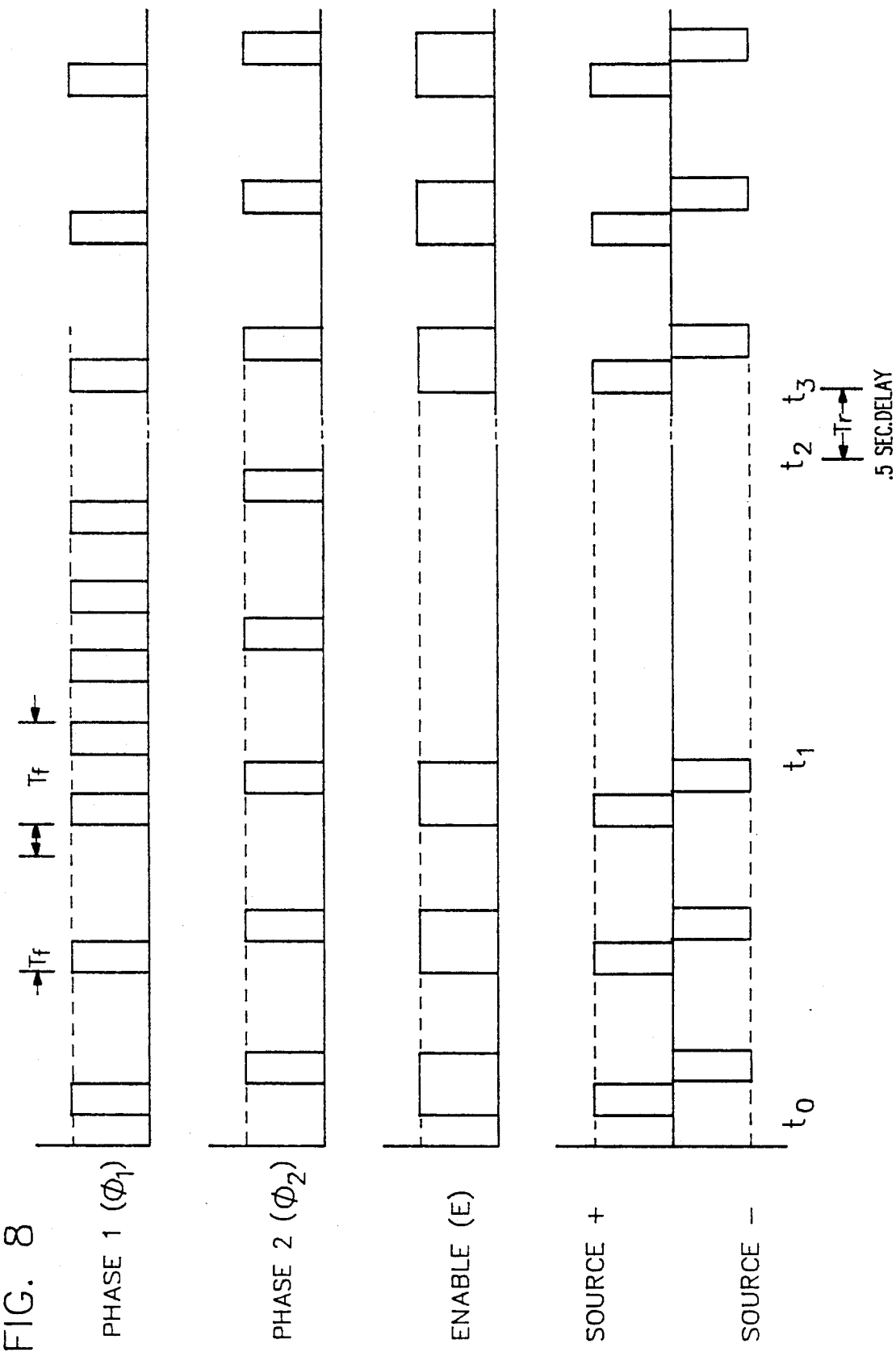

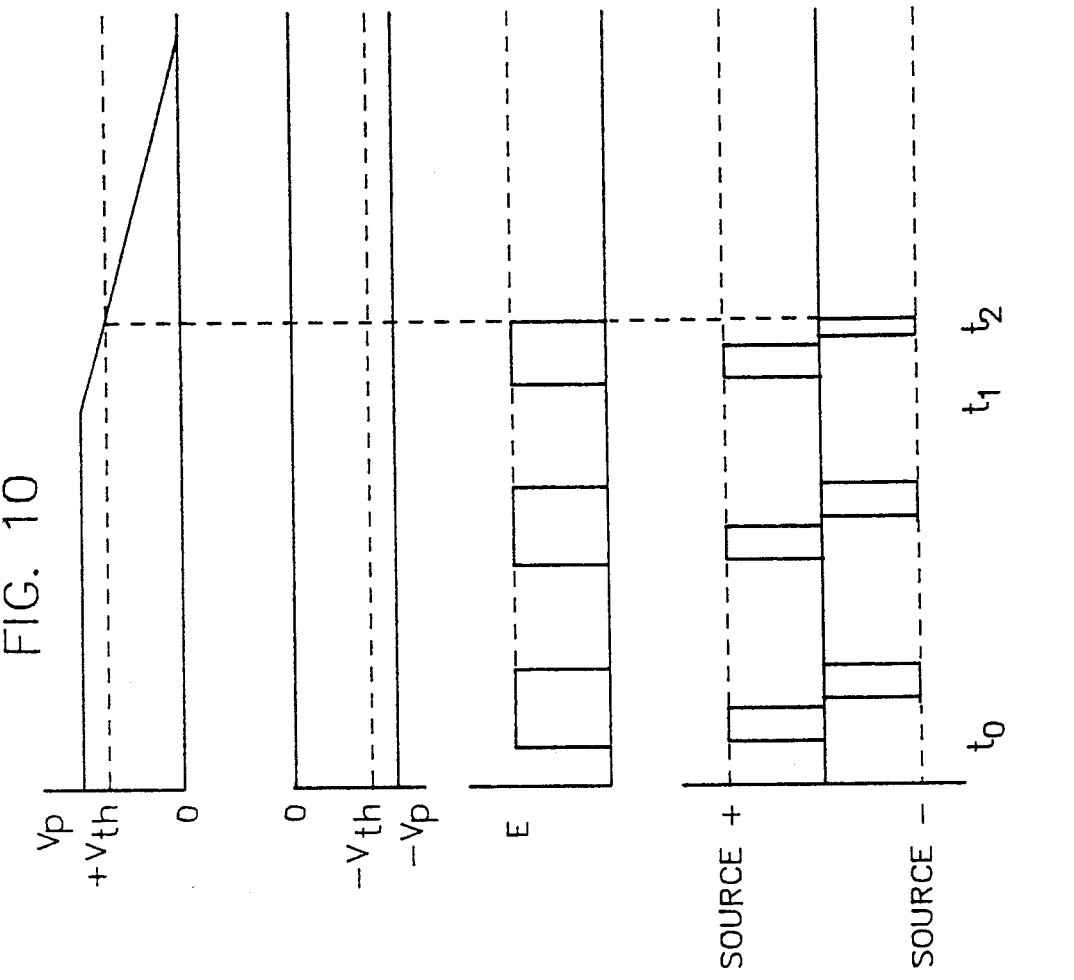

POWER SUPPLIES

RELATION TO OTHER APPLICATIONS

This application is a continuation-in-part of application Ser. No. 528,059 filed 23 May 1990 for DETECTORS. It is also a continuation-in-part of application Ser. No. 598,984 filed 17 Oct. 1990 for INFRARED RADIATION SOURCES.

TECHNICAL FIELD OF THE INVENTION

In one respect the present invention relates to power supplies and, more particularly, to novel, improved power supplies of the bipolar type.

In a second aspect, the present invention relates to non-dispersive infrared radiation (NDIR) gas analyzers which have infrared radiation emitters driven by bipolar power supplies embodying the principles of the present invention.

BACKGROUND OF THE INVENTION

U.S Pat. Nos. 4,859,858 and 4,859,859, both entitled GAS ANALYZERS, were issued to Knodle et al. on 22 Aug. 1989. These patents disclose state-of-the-art apparatus for outputting a signal indicative of the concentration of a designated gas in a sample being monitored by the apparatus. These patents are hereby incorporated by reference thereto into this application.

The gas analyzers disclosed in the '858 and '859 patents are of the non-dispersive type. They operate on the premise that the concentration of a designated gas can be measured by: (1) passing a beam of infrared radiation through the gas, and (2) then ascertaining the level of the attenuated energy in a narrow band absorbable by the designated gas. This done with a detector capable of generating a concentration proportional electrical output signal.

One important application of the invention at the present time is in capnometers for monitoring the level of carbon dioxide in the breath of a medical patient. This is typically done during a surgical procedure as an indication to the anesthesiologist of the patient's condition. As the patient's well being, and even his life, is at stake, it is of paramount importance that the carbon dioxide concentration be measured with great accuracy.

In a typical instrument or system employing non-dispersive infrared radiation to measure gas concentration, including those disclosed in the '858 and '859 patents, the infrared radiation is emitted from a source and focused by a mirror on the gases being analyzed. After passing through the body of gases, the beam of infrared radiation passes through a filter. That filter absorbs all of the radiation except for that in a narrow band centered on a frequency which is absorbed by the gas of concern. This narrow band of radiation is transmitted to a detector which is capable of producing an electrical output signal proportional in magnitude to the magnitude of the infrared radiation impinging upon it. Thus, the radiation in the band passed by the filter is attenuated to an extent which is proportional to the concentration of the designated gas. The strength of the signal generated by the detector is consequently inversely proportional to the concentration of the designated gas and can be inverted to provide a signal indicative of that concentration.

The NDIR gas analyzers disclosed in the '858 and '859 patents employ an infrared radiation emitter which has a layer of an electrically resistive, emissive material on a substrate fabricated from a material with low thermal conductivity such as steatite.

For a gas analyzer of the NDIR type to operate efficiently, the infrared radiation passed through the gas undergoing analysis must be of a modulated or pulsed character. That is, it must be made available as a stream of pulses rather than in the form of a continuous beam. Otherwise, the signal-to-noise ratio of the electrical signal available from the analyzer will typically not be high enough for the signal to be useful.

Two methods for supplying modulated infrared radiation to the environment in which sampling occurs have heretofore been proposed. One employs a mechanical chopper to create the wanted stream of pulses from a continuous beam of energy outputted by the infrared radiation source. A chopper has a spinning wheel between the infrared radiation source and the detector. The wheel has a series of apertures spaced equally around its periphery. Consequently, as the wheel rotates, the transmission of the attenuated beam of infrared radiation to the detector of the gas analyzer is alternately enabled and interrupted, typically at a frequency of less than one hundred cycles per second.

Gas analyzers of the character just described are disclosed in U.S. Pat. No. 3,793,525 issued Feb. 19, 1974, to Burch et al. fir DUAL-CELL NON-DISPERSIVE GAS ANALYZER; U.S. Pat. No. 4,811,776 issued May 21, 1974, to Blau, Jr. for GAS ANALYZER; U.S. Pat. No. 3,987,303 issued Oct. 19, 1976, to Stoft et al. for MEDICAL ANALYTICAL GAS DETECTOR; U.S. Pat. No. 4,011,859 issued Mar. 15, 1977, to Frankenberger for METHOD FOR CONTINUOUSLY MEASURING THE $CO_2$ CONTENT IN BREATHING GAS; U.S. Pat. No. 4,204,768 issued May 27, 1980, to N'Guyen for GAS ANALYZERS OF THE SELECTIVE RADIATION ADSORPTION TYPE WITH A CALIBRATION CELL; U.S. Pat. No. 4,268,751 issued May 19, 1981, to Fritzlen et al. for INFRARED BREATH ANALYZER; AND U.S. Pat. No. 4,371,785 issued Feb. 1, 1983, to Pedersen for METHOD AND APPARATUS FOR DETECTION OF FLUIDS and in a Reliable, Accurate $CO_2$ Analyzer for Medical Use, Solomon, HEWLETT-PACKARD JOURNAL, Sep. 1981, pages 3-21.

Gas analyzers with mechanical choppers have a number of drawbacks. They are bulky, heavy, and expensive; have moving parts, which is undesirable; and also have complex optical designs. They also tend to be less accurate than is desirable and to lack long term stability.

Also, gas analyzers employing mechanical choppers are relatively fragile. For example, they will typically not work properly, if at all, after they are dropped.

A second, and we believe superior, method of generating the necessary modulated infrared radiation is to drive the infrared radiation emitter with a power supply which applies pulses of electrical energy to the emitter. In an NDIR analyzer with the type of infrared radiation emitter described above, an emissive layer of the emitter heats up and emits a pulse of infrared radiation when a pulse of electrical energy is applied to that layer by the power source. Thereafter, the emissive layer rapidly cools down. Therefore, in the remainder of the emitter duty cycle, radiation in the infrared portion of the spectrum is not outputted from the emitter to any appreciable extent.

This modulation technique has the advantage of eliminating mechanical systems and components along with the attendant bulk, weight, complexity, and fragility of those devices. Also, the pulsed power supply approach tends to be significantly more accurate than the mechanical chopper technique.

Heretofore, the power supplies used for the purposes just discussed and in similar applications supplied unipolar pulses of controlled magnitude, duration, and frequency to the driven emitter—that is, a stream of pulses all having either a positive (or negative) value. As a result, pulsed emitters tend to have an important disadvantage common to schemes employing mechanical choppers, a lack of long-term stability. This is a result of the operating current always flowing in the same direction through the emitter and producing strong electrical fields. These, because they are all oriented in the same direction, cause migration of the emitter materials over time. The consequence of that migration is degraded performance and, ultimately, failure of the emitter.

SUMMARY OF THE INVENTION

We have now discovered that the just-described and unwanted migration of materials in those infrared radiation emitters having an emissive layer on a compatible substrate can be avoided by employing a bipolar power source, instead of a unipolar one, to drive the emitter of an infrared radiation source. By doing so, the electrical fields created in the vicinity of the emitter are reversed each time operating voltage is applied to the emitter; and the tendency of the emitter materials to migrate is eliminated.

Yet another advantage of employing a bipolar power supply to operate an infrared radiation emitter of the character described above is that more power can be applied to the emissive component of the emitter; i.e., higher current densities can be employed. This is important because the result is increased emitter output.

Also, higher frequencies can be employed. And, because migration ceases to be a significant problem, emitter materials heretofore ruled out because of suspectibility to migration but otherwise desirable can be employed For the exemplary NDIR application discussed above, the bipolar power supply is designed to output pulses at a frequency in the range of 40 to 250 Hz and at a voltage in the range of 12 to 24 V with the pulse taking up from 5 to 20 percent of the duty cycle.

Major components of the power supply are: a driver which supplies the positive and negative pulses; timing circuits that control the frequency with which the pulses are outputted by the driver; watchdog circuits for shutting down the driver if a fault occurs; and a reset circuit which delays subsequent restarting of the driver once the fault is cleared. The reset circuit allows the timing and other circuits of the power supply to stabilize before the outputting of emitter operating pulses is resumed.

The novel power supplies disclosed herein also have the advantage that they can be used in many applications other than the one just described. For example, the infrared emitters of thermal printers have the same material migration problem as the emitters cf gas analyzers. This problem can similarly be solved by substituting a bipolar power supply of the character described herein for the unipolar power supplies heretofore employed to drive a thermal print head.

Still other applications of the present invention, many not involving the operation of infrared radiation emitters, will be readily apparent to those to whom this specification is directed.

OBJECTS OF THE INVENTION

From the foregoing, it will be apparent to the reader that one important and primary object of the invention resides in the provision of novel, improved, electronic power supplies.

A related and also important object of the invention resides in the provision of power supplies which have a bipolar mode of operation in that they are capable of outputting pulses which alternate in polarity.

An object which is also important and related to the previous one resides in the provision of bipolar power supplies which can be used to advantage in a variety of applications.

Still another related and important object of the invention is the provision of electronic power supplies which can be employed to particular advantage to drive infrared radiation emitters, especially those with a substrate supporting a layer of an emissive, electrically resistive material.

Yet another important object of the invention is the provision of novel methods of operating the infrared radiation emitters of gas analyzers and other devices and systems, those methods involving the application of pulses which alternate in polarity to the emissive element of the emitter.

Still other important objects and features and additional advantages of the invention will be apparent to the reader from the foregoing and the appended claims and as the ensuing detailed description and discussion proceeds in conjunction with the accompanying drawing.

BRIEF DESCRIPTION OF THE DRAWINGS

In the drawing:

FIGS. 7-10 are timing diagrams which facilitate an understanding of the manner in which the power supply operates.

DETAILED DESCRIPTION OF THE INVENTION

Figure 1:
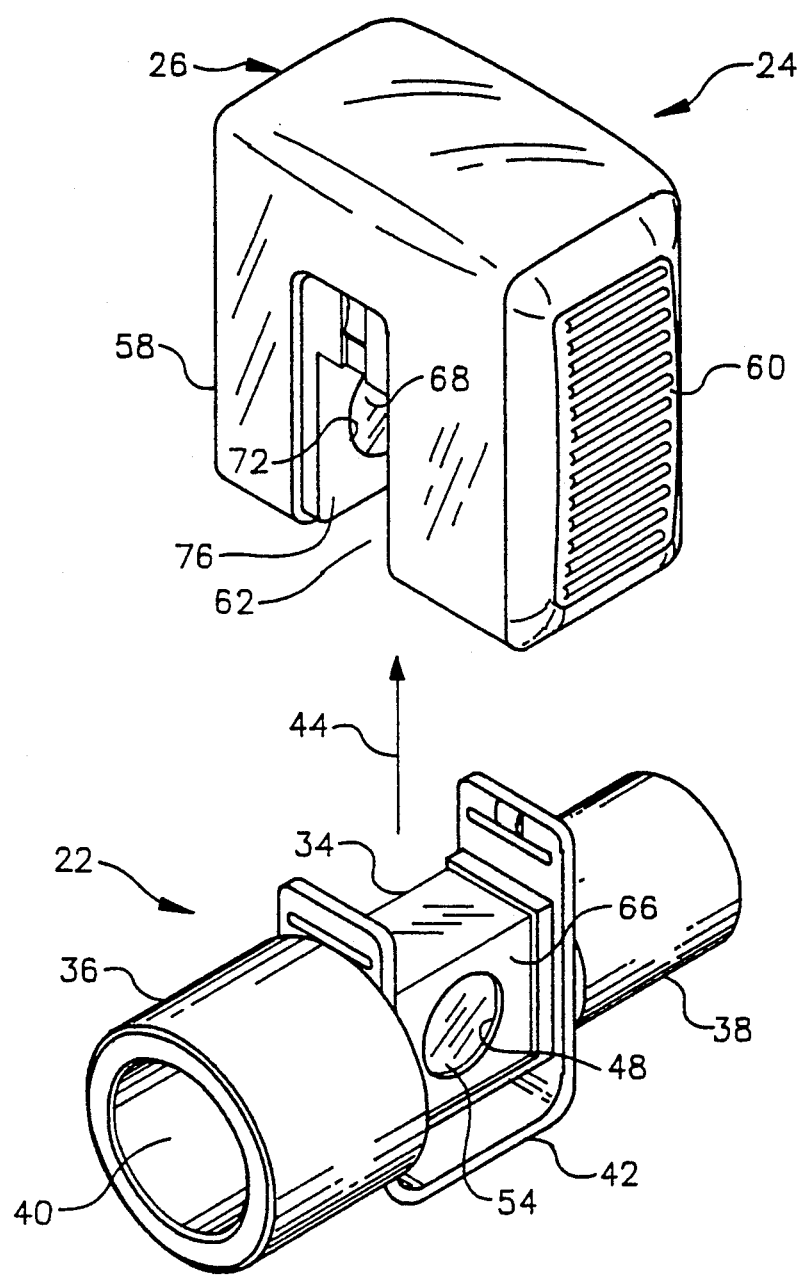
FIG. 1 is an exploded view of: (a) an airway adapter which provides a particularized flow path for a gas being analyzed, and (b) a transducer which outputs a signal indicative of the concentration of the designated gas and a reference signal; that transducer includes an infrared radiation emitter driven by a bipolar power supply constructed in accord with the principles of the present invention.

The principles of the present invention can be employed to particular advantage in transducers for outputting: (a) a signal proportional in magnitude to the concentration of carbon dioxide flowing through an airway adapter in a patient-to-mechanical ventilator circuit, and (b) a reference signal. These signals can be ratioed in the manner disclosed in above-incorporated U.S. Pat. Nos. 4,859,858, and 4,859,859 to provide a third signal accurately and dynamically representing the concentration of the carbon dioxide flowing through the airway adapter. A representative and preferred airway adapter and a complementary transducer constructed in accord with, and embodying, the principles of the present invention are shown in FIGS. 1 and 2 and respectively identified by reference characters 22 and 24.

Figure 2:
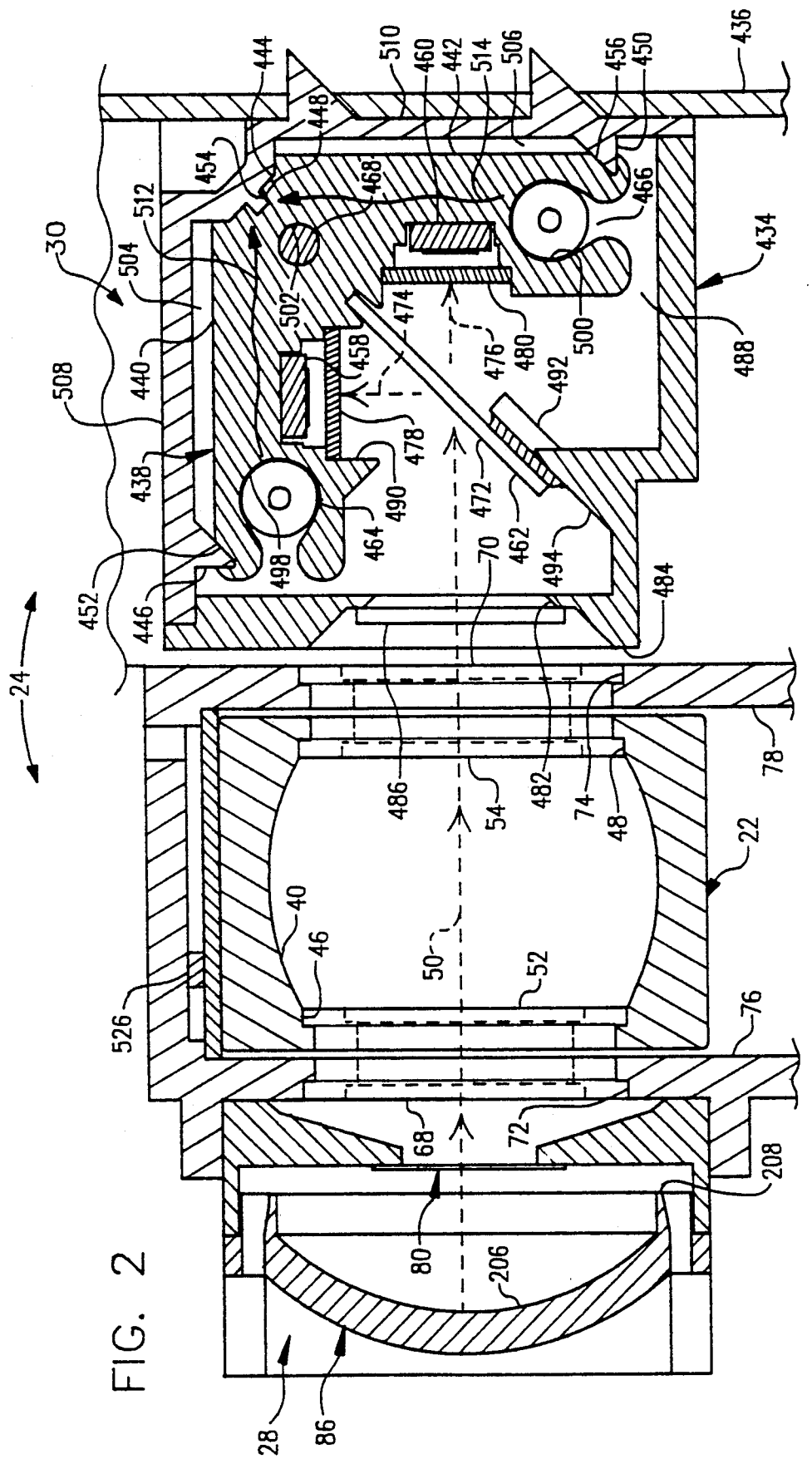
FIG. 2 is a section through, and depicts, an infrared radiation source- and detector-incorporating optical system of the airway adapter/transducer assembly.
Figure 2A:
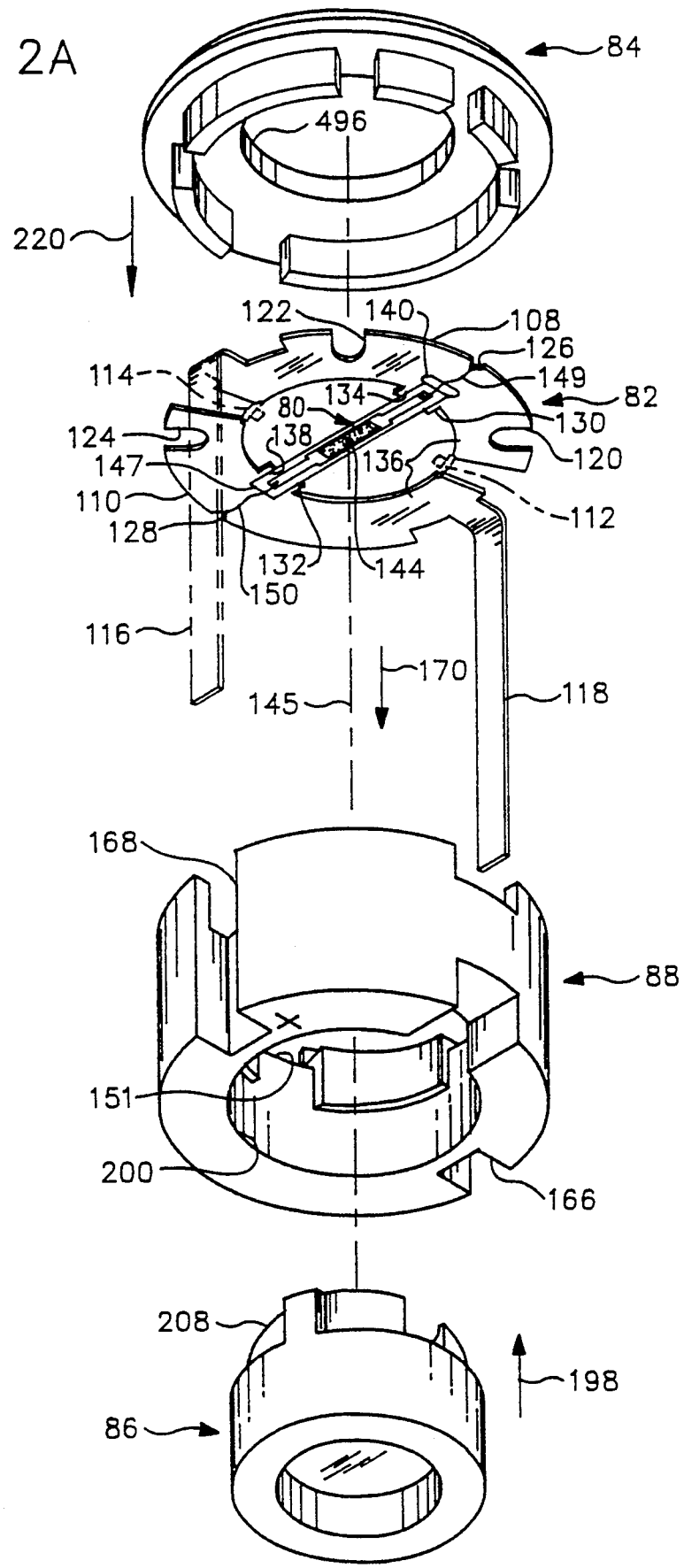
FIG. 2A is an exploded view of the infrared radiation source.
Figure 3:
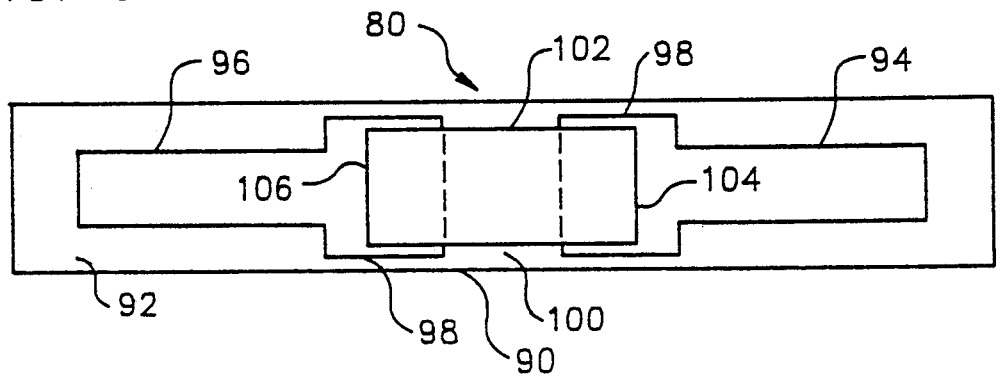
FIG. 3 is a plan view of an emitter incorporated in the infrared radiation source.
Figure 4:
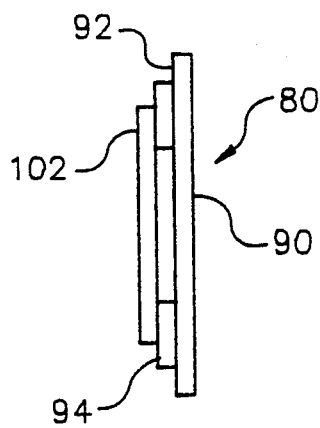
FIG. 4 is an end view of the emitter.
Figure 6:
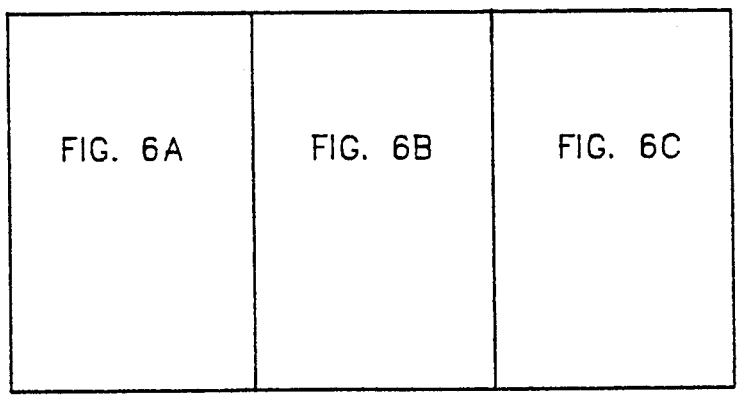
FIG. 6 shows the relationship among FIGS. 6A, 6B, and 6C which together constitute a schematic diagram of the bipolar power supply.

FIG. 1 shows primarily the polymeric housing or casing 26 of transducer 24. This transducer also includes: (a) an infrared radiation emitter unit or source 28 (FIGS. 2A, 3, and 4); (b) a detector unit 30 (FIG. 2); (c) a detector unit power supply 32 (FIG. 1-1); and (d) a bipolar power supply 33 (FIGS. 5 and 6) for infrared radiation source 28.

The illustrated airway adapter 22 is designed for connection between an endotracheal tube inserted in a patient's trachea and the plumbing of a mechanical ventilator (neither shown), and transducer 24 is in this instance employed to measure the expired carbon dioxide level of a medical patient.

The particular airway adapter 22 illustrated in FIG. 1 is not, by itself, part of the present invention. Consequently, it will be described herein only to the extent necessary for an understanding of the present invention.

Referring then to FIG. 1, airway adapter 22 is a one piece unit typically molded from Valox polyester or a comparable polymer. Airway adapter 22 has a general parallelepipedal center section 34, two cylindrical end sections 36 and 38, and a sampling passage 40 extending from end-to-end through the adapter.

The central section 34 of airway adapter 22 provides a seat for transducer 24. An integral, U-shaped casing element 42 positively locates transducer 24 endwise of the adapter and, also, in that transverse direction indicated by arrow 44 in FIG. 1. That arrow also shows the direction in which airway adapter 22 is displaced to assemble it to transducer 24.

Apertures 46 and 48 are formed in the center section 34 of airway adapter 22. With transducer 24 assembled to the airway adapter, these apertures are aligned along an optical path identified by reference character 50 in FIG. 2. That optical path extends from the infrared radiation emitter unit 28 in transducer 24 transversely across airway adapter 22 and the gas(es) flowing through sampling passage 40 to the infrared radiation detector unit 30 of transducer 24.

To: (a) keep the gases flowing through airway adapter 22 from escaping through apertures 46 and 48 without attenuating the infrared radiation traversing optical path 50, and (b) keep foreign material from the interior of the airway adapter, the apertures are sealed by sapphire windows 52 and 54. Sapphire windows are employed because other materials such as glass or plastic would absorb the infrared radiation to an extent that would significantly degrade the quality of the signals generated in detector unit 30.

That casing 26 of transducer 24 in which the infrared radiation source 28 and detector unit 30 are housed has left-hand and right-hand end sections 58 and 60 with a rectangular gap 62 therebetween. With the transducer assembled to airway adapter 22, the two sections 58 and 60 of transducer casing 26 embrace those two inner side walls 64 and 66 of the airway adapter central section 34 in which energy transmitting windows 52 and 54 are installed.

Optically transparent, typically sapphire, windows 68 and 70 are installed along optical path 50 in apertures 72 and 74 through the inner end walls 76 and 78 of transducer housing 26. These windows allow infrared radiation outputted by unit 28 in the left-hand end section 58 of transducer housing 26 to pass to airway adapter 22 and from the airway adapter to the detector unit 30 in the right-hand section 60 of the transducer housing. At the same time, windows 68 and 70 keep foreign material from penetrating to the interior of the transducer casing.

Referring now to FIGS. 2A, 3, and 4, the unit 28 employed to emit infrared radiation, to form that energy into a beam, and to propagate the beam along optical path 50 includes: an infrared radiation emitter 80, a commutator 82, a tube or cap 84, and a mirror component 86, all supported from a base 88.

Infrared emitter or energy source 80, best shown in FIGS. 3 and 4, is of a unique thick film construction. It has a substrate 90 which, in one actual embodiment of the invention, is 0.250 inch long, 0.040 inch wide, and 0.005 inch thick. This substrate can range in thickness from 0.003 to 0.005 in., and it is formed from a material having low thermal conductivity. Steatite (a polycrystalline material containing magnesium oxide and silicon dioxide) is preferred because it has a thermal conductivity which is on the order of one magnitude less than conventional low thermal conductivity materials such as alumina. This is important because the low thermal conductivity material significantly reduces the power required to heat the emitter to its operating temperature.

However, alumina can be employed instead of steatite. It if is, the substrate is preferably coated with a film of a dielectric material having low thermal conductivity such as a dielectric glass.

Another substrate material that can be employed is fused silica.

Bonded to the upper surface 92 of substrate 90 are two T-shaped electrical conductors or terminals 94 and 96. In the exemplary infrared radiation emitter 80 illustrated in FIGS. 3 and 4, the head 98 of each conductor is 0.020 inch long; and the gap 100 between the conductors is 0.030 inch.

Terminals 94 and 96 are preferably formed of a platinum and gold containing cermet obtained by printing an ink such as DuPont's 4956 on the surface 92 of substrate 90 and then firing the substrate.

Superimposed on terminals 94 and 96 and bonded to the upper surface 92 of substrate 90 with its ends overlapping conductors 94 and 96 is a thick film or layer 102 of an emissive, electrically resistive material. The preferred material is obtained by firing Electro-Science Labs ESL3812 Ink. This ink contains a major proportion of platinum and has an operating temperature in the range of 250–300 degrees centigrade.

The illustrated, exemplary, emissive layer 102 is 0.070 inch long; and the two ends 104 and 106 of the emitter overlap 0.020 inch onto the conductor 94 and the conductor 96 of emitter 80. Thus, the total overlap constitutes 57 percent of the total area of emissive layer 102. This is within the preferred and operable range of 50 to 60 percent.

Overlaps in the range just described tend to keep the current density at the interfaces between emissive layer 102 and conductors 94 and 96 from becoming too high and causing emitter 80 to fail by burnthrough or fatigue cracking of the emissive layer.

That we can thus prevent failures of emitter 80 is surprising. Heretofore, it has been believed that successful performance of a thick film device with an active layer-to-conductor overlap could not be obtained with an overlap exceeding about 15 percent.

Also contributing to the resistance to failure from exposure to excessive current densities is the T-shaped configuration of conductors 94 and 96. This is at least potentially superior to the more conventional rectangular o straight sided conductors as far as resistance to emissive layer burnthrough is concerned.

It is one of the important features of the present invention that the emissive layer 102 and substrate 90 of emitter 80 are so constructed and related in the manner described in parent application Ser. No. 598,984 as to optimize the performance of the emitter as the emissive layer is periodically heated to produce the wanted emission of radiant energy.

Referring now more specifically to FIG. 2A, commutator 82 is stamped from a sheet of conductive metal such as tin plated copper. The emitter has two, generally similar, arcuate segments 108 and 110 connected by integral tabs 112 and 114; a conductor or 10 terminal 116 integral with and extending radially from segment 108; and a second conductor or terminal 118 which is integral with and extends radially from commutator segment 110 in the opposite direction at a location halfway around the circumference of the commutator from terminal 116.

U-shaped alignment slots 120 and 122 open onto the periphery of segment 108, and a third, U-shaped alignment slot 124 opens onto the periphery of segment 110. Also opening onto the peripheries of commutator segments 108 and 110, respectively, are conductor receiving slots 126 and 128.

Additionally found in commutator 82 are emitter supports 130 and 132. Support 130 is integral with, and extends radially inward from, commutator segment 110 Emitter support 132 is axially aligned with support 130. It is integral with, and extends radially inward from, commutator segment 108. Emitter support 130 has an emitter receiving recess 134 on the bottom side 136 of commutator 82; and a second emitter receiving recess 138 is formed in emitter support 132, also on the bottom side 136 of commutator 82.

One end 140 of emitter 80 is seated in emitter support recess 134 and bonded in place as by epoxy adhesive. By way of surface tension, the epoxy adhesive draws emitter 80 into a position in which the midpoint 144 of emitter layer 102 coincides with the centerline 145 of emitter unit 28. This is important in that it optimizes the ability of mirror assembly 86 to collate and focus the energy emitted from layer 102; and this results in an optical beam of optimum quality being projected from emitter unit 28.

The opposite end 147 of the emitter is seated in the slot 138 in emitter support 132. However, emitter 80 is not bonded to that support but is, instead, free to move back and forth in the slot. As a consequence, when the emitter 80 grows or increases in length due to thermal expansion, this expansion is accommodated rather than being constrained. As a consequence, the stresses which would be imposed upon emitter 80 if both ends were fixed are avoided, eliminating the damage to emitter 80 or complete failure of that component which might result if mechanical stresses were imposed upon it.

After emitter 80 has been assembled to commutator 82, the two emitter terminals 94 and 96 are respectively connected to conductive segments 108 and 110 of the commutator 82. Electrical conductors or leads 149 and 150 soldered at opposite ends to the emitter unit terminals 94 and 96 and commutator segments 108 and 110 are employed for this purpose.

Once the steps just discussed have been completed, commutator terminals 1 16 and 118 are bent at right angles to the conductor segments 108 and 110 of the commutator, and the emitter or commutator assembly is installed in the base 88 of radiant energy emitting unit 28. This component is a monolithic member. The environment in which it operates can reach an elevated temperature due to the heating of the environment by the emissive layer 102 of emitter 80. .The base is therefore fabricated of a polysulfone or comparable polymer which will remain structurally stable at the temperatures it reaches during the operation of emitter unit 28 and as leads 149 and 150 are soldered to base-supported commutator segments 108 and 110.

Base 88 has: a cylindrical configuration; an internal platform 151, an asymmetrical array of bosses (not shown) configured to complement corresponding ones of the three U-shaped slots 120, 122, and 124 in the segments 108 and 110 of commutator 82; and diametrically opposed slots 166 and 168 into which commutator terminals 116 and 118 are fitted. The asymmetrical relationship of the radially oriented bosses on base 88 and the complementary notches 120 . . . 124 of commutator 82 keeps the commutator/emitter assembly from being installed upside down in base 88.

The assembly of emitter 80 and commutator 82 is installed in base 88 by aligning it relative to the base and then displacing the emitter/commutator assembly downwardly in the direction indicated by arrow 170 until the segments 108 and 110 of the commutator are seated on base platform 151. The emitter/commutator assembly is retained in place by an appropriate adhesive.

After the emitter/commutator assembly is installed and bonded to base 88, the two commutator tabs 112 and 114 are removed, leaving gaps between the commutator segments 108 and 110. This electrically isolates commutator segment 108 from segment 110. Therefore, current supplied to one of the commutator terminals 116 and 118 flows from the associated commutator segment 108 or 110 through emitter 80 and the second commutator segment to the second of the two commutator terminals.

Once the emitter/commutator assembly has been installed in and bonded to base 88 and tabs 112 and 114 removed, emitter unit tube or cap 84 is installed. This component is an annular member fabricated from a polymer with a high degree of structural stability such as acrylonitrile-butadiene-styrene (ABS).

Cap 84 is of the same diameter as base 88. It is installed by displacing it relative to base 88 in the direction indicated by arrow 198 in FIG. 2A. An appropriate, but unillustrated, adhesive is employed to secure cap 84 to base 88.

The remaining step in putting together emitter unit 28 is to install component or mirror assembly 86 in base 88.

The mirror assembly, best shown in FIGS. 2 and 2A, is a monolithic member with a circular cross section.

The mirror assembly, also typically fabricated from ABS, is dimensioned to fit within the circular central bore 200 of emitter base 88. A parabolic surface 206 is formed in the upper side 208 of the assembly. Parabolic surface 206 is first plated with copper and then overplated with gold. This provides a parabolic mirror for collating and focusing the infrared radiation from emitter 80.

Mirror assembly 86 is installed in base 88 by moving it relative to the base as indicated by arrow 220 in FIG. 2A. As in the case of cap 84, an appropriate but not illustrated adhesive can be employed to hold the mirror assembly in place.

Figure 5:
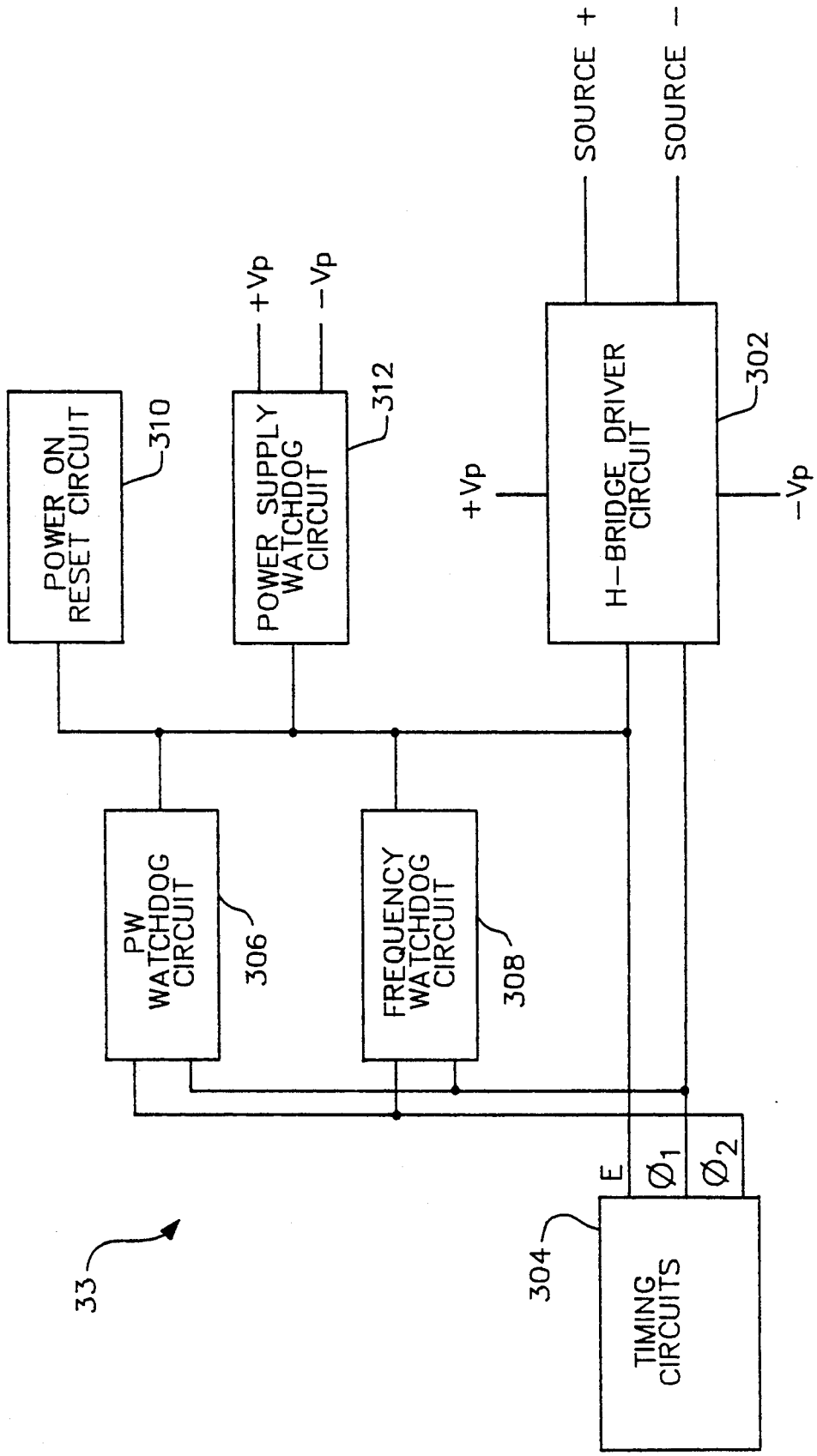
FIG. 5 is a block diagram of the bipolar power supply.

The bipolar power supply 33 employed to drive the emitter 80 of infrared source unit 28, shown in block diagram form in FIG. 5, includes an H-bridge driver circuit 302, timing circuits collectively identified by reference character 304, pulse width and frequency watchdog circuits 306 and 308, a power on reset circuit 310, and a power supply watchdog circuit 312.

The load, emitter 80 of infrared source unit 28, is connected across the outputs of H-bridge driver circuit 302. These outputs are identified as SOURCE+ and SOURCE− in FIG. 5.

Circuits 304 supply timing signals to driver 302. The timing signals are derived from a crystal oscillator (not shown) and then counted down to provide the desired pulse rate and duty cycle. A current implementation uses a 7 megahertz oscillator to provide an 85.45 Hz pulse rate at a 7.1% duty cycle (this value is the part of the duty cycle in which both one positive signal and one negative signal are outputted). The timing circuits are not, by themselves, part of the present invention. Accordingly, they will be described herein only to the extent necessary for an understanding of the present invention.

Timing circuits 304 provide three signals to driver circuit 302: (1) PHASE 1 ($\phi_1$), a series of pulses basically corresponding to the time during which the driver circuit generates the positive output signal SOURCE+; (2) PHASE 2 ($\phi_2$), a series of pulses basically corresponding to the time period during which the driver circuit generates the negative output signal SOURCE−; and (3) ENABLE (E), a signal that must be present for the driver circuit to generate the positive and negative source voltages SOURCE+ and SOURCE−.

Positive input voltage $+V_p$ and negative input voltage $-V_p$ signals are also supplied to driver circuit 302. Based on the PHASE 1 ($\phi_1$), PHASE 2 ($\phi_2$) and ENABLE (E) signals provided by the timing circuits, the driver circuit 302 generates bipolar outputs SOURCE+ and SOURCE−, which are derived from the input voltage signals $+V_p$ and $-V_p$.

The signals PHASE ($\phi_1$) and PHASE 2 ($\phi_2$) are also supplied to pulse width watchdog circuit 306 measures the width of each pulse of both the PHASE 1 ($\phi_1$) and the PHASE 2 ($\phi_2$) signals. If the width of any pulse of either the PHASE 1 ($\phi_1$) or the PHASE 2 ($\phi_2$) signals exceeds a predetermined value, the pulse width watchdog circuit 306 forces the ENABLE (E) signal LOW, thereby preventing the driver circuit from generating an output voltage.

Power supply watchdog circuit 312 monitors the input voltages $+V_p$ and $-V_p$ of the signals supplied to driver circuit 302. The power supply watchdog circuit 312 shuts off the ENABLE (E) signal, preventing the driver circuit 302 from generating an output voltage, if the positive input voltage $+V_p$ falls below a positive threshold value $+V_{th}$ or the negative input voltage $-V_p$ exceeds a negative threshold value $-V_{th}$.

When any of the watchdog circuits determines that a fault condition requiring the shutdown of the driver circuit 302 exists, the appropriate watchdog circuit forces the ENABLE (E) signal LOW, thereby shutting off the driver circuit 302 for as long as the fault exists. When the fault condition clears the appropriate watchdog circuit no longer suppresses the ENABLE (E) signal. However, the power-on reset circuit 310 delays reinstatement of the ENABLE (E) signal to a HIGH condition to allow the timing circuits and other circuitry to become stable before the driver circuit 302 begins generating source voltages.

Figure 6A:
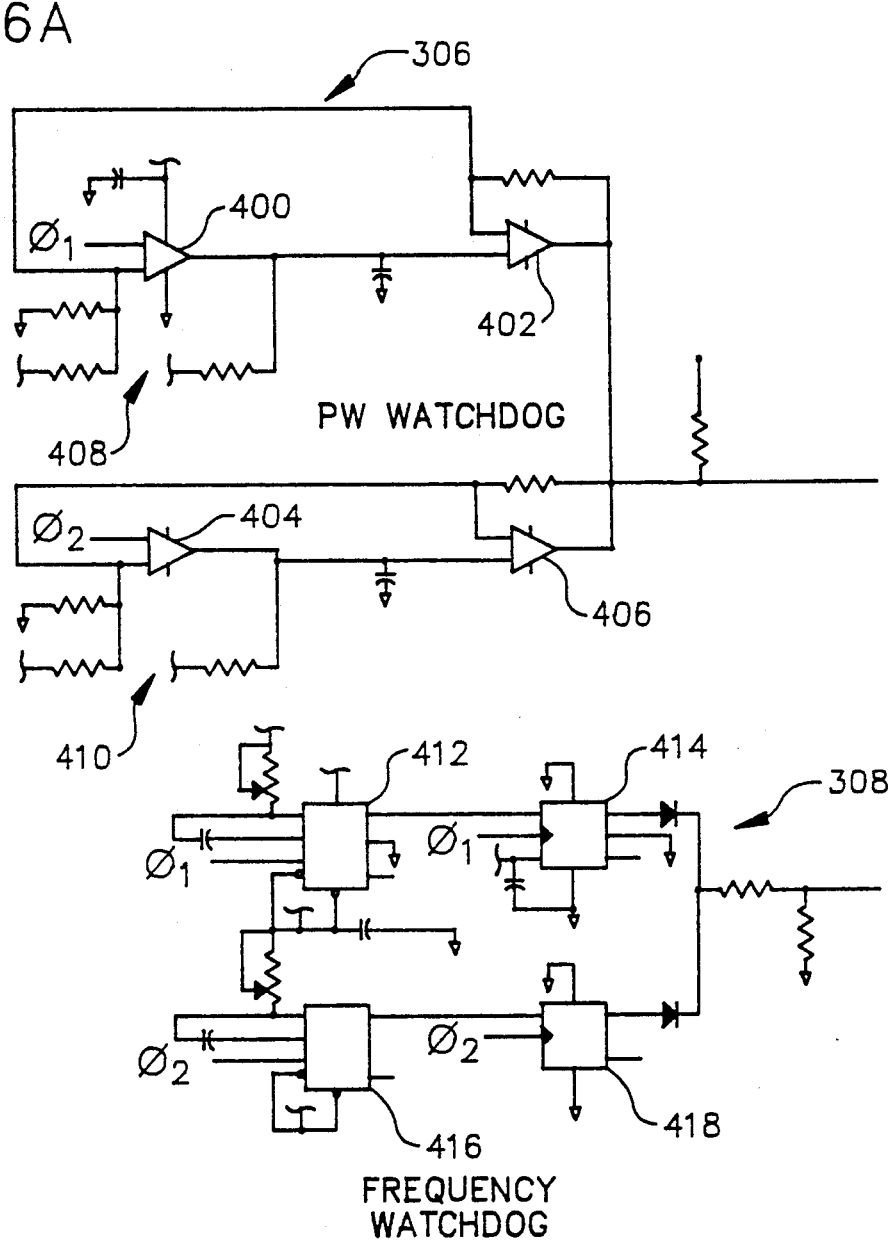
Figure 6C:
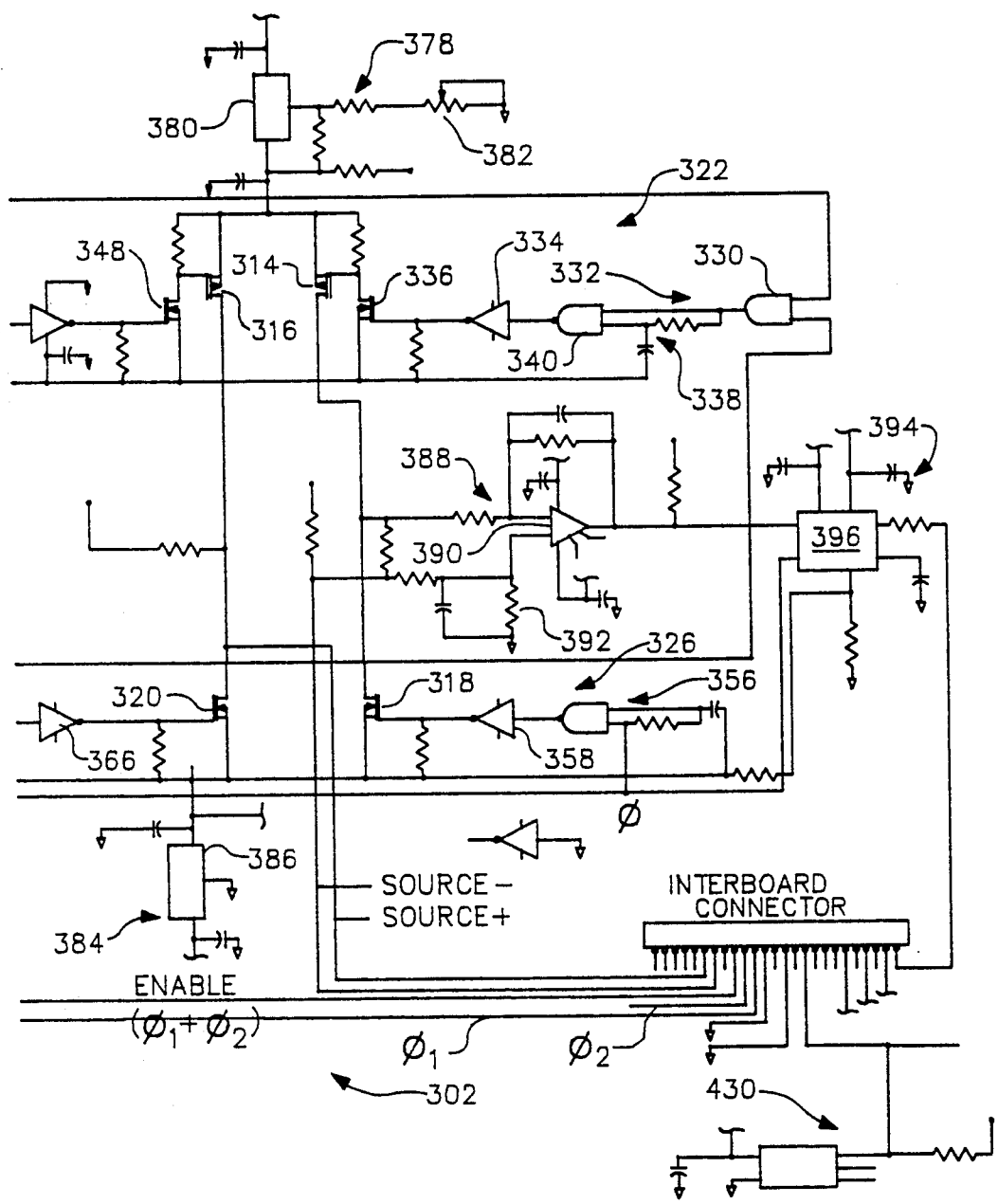

As shown in FIGS. 6B and 6C, driver circuit 302 contains power MOSFETs 314, 316, 318, and 320 arranged in an H-bridge configuration. MOSFET drive circuits 322, 324, 326, and 328 control MOSFETs 314, 316, 18, and 320, respectively.

MOSFET drive circuit 322 consists of AND gate 30, turn-on delay circuit 332, inverter 334, and a MOSFET 336. Turn-on delay circuit 332 comprises parallel RC circuit 338 and NAND gate 340.

MOSFET drive circuit 324 consists of AND gate 342, turn-on delay circuit 344, inverter 346, and MOSFET 348. Turn-on delay circuit 344 includes parallel RC circuit 350 and NAND gate 352.

MOSFETS 336 and 348 are for translating the outputs of inverters 334 and 346 into signals appropriate for controlling MOSFETS 314 and 316, respectively.

MOSFET drive circuit 326 includes turn-on delay circuit 356 and inverter 358. Turn-on delay circuit 356 includes a parallel RC circuit 360 and NAND gate 362.

MOSFET drive circuit 328 includes a turn-on delay circuit 364 and inverter 366. Turn-on delay circuit 364 consists of parallel RC circuit 368 and NAND gate 370.

Signals ENABLE, PHASE 1 ($\phi_1$), and PHASE 2 ($\phi_2$) and all voltages for powering drive circuit 302 are externally provided. The ENABLE signal enters the circuit through transistor 372, while the PHASE 1 ($\phi_1$) signal enters through transistor 374.

Signals ENABLE (E) and the inverse of the PHASE 1 ($\phi_1$) signal, which is generated by inverter 376 and identified as $\overline{\text{PHASE 1 } (\phi_1)}$ applied to the inputs of AND gate 330. The ENABLE signal and the PHASE 1 ($\phi_1$) signal are applied to the inputs of AND gate 342. Thus, pulses cannot be outputted by driver circuit 302 unless the ENABLE (E) signal is HIGH. The PHASE 1 ($\phi_1$) signal and its inverse $\overline{\text{PHASE 1 } (\phi_1)}$ are also applied to turn-on delay circuits 156 and 164, respectively.

Turn-on delay circuit 332 includes an RC circuit 338 and a NAND gate 340. The output of AND gate 330 is sent directly to one input terminal of NAND gate 340 and to the other input terminal via RC circuit 338. Since RC circuit 338 delays the rise of the output of AND gate 330, NAND gate 340 goes HIGH a short period $T_d$ after AND gate 330.

Turn-on delay circuit 332 thus delays slightly the changing of the output of AND gate 330 from an OFF state to an ON state. The change of the output of AND gate 330 from an ON state to an OFF state is basically unaffected by turn-on delay circuit 332.

Inverter 334 renders the polarity of the output from NAND gate 340 appropriate for driving MOSFET 336 to turn on MOSFET 314.

MOSFET drive circuit 324 operates in the same manner as MOSFET drive circuit 322 and will not be discussed in detail. It is sufficient in this respect to point out that, as the PHASE 1 ($\phi_1$) signal is directly applied to the input of its AND gate 342, MOSFET drive circuit 324 turns on MOSFET 316 only when MOSFET 314 is turned off.

MOSFET drive circuits 326 and 328 operate in basically the same manner as MOSFET drive circuits 322 and 324, differing only in the following respects. First, because the sources of MOSFETs 320 and 318 are connected to a negative potential, inverters 358 and 366 of circuits 326 and 328 directly drive MOSFETs 318 and 320, respectively, without a translating device such as the MOSFETs 336 and 348 used in MOSFET drive circuits 322 and 324, respectively. Second, AND gates corresponding to AND gates 330 and 342 in MOSFET drive circuits 322 and 324 are not used in MOSFET drive circuits 326 and 328. These AND gates are omitted because turning off MOSFETS 314 and 316 with the ENABLE (E) signal is sufficient to turn off the entire drive circuit 302.

As will be apparent to the reader from the foregoing, MOSFET drive circuits 322, 324, 326, and 328: (a) turn on MOSFETs 316 and 318 and turn off MOSFETs 314 and 320, thus supplying the SOURCE− signal during a PHASE 2 ($\phi_2$) pulse; (b) turn on MOSFETs 314 and 320 and turn off MOSFETs 316 and 318 consequently supplying the SOURCE+ signal during a PHASE 1 ($\phi_1$) pulse; and (c) turn off MOSFETs 314 and 316 whenever the ENABLE (E) signal goes LOW.

MOSFETs 314 and 316 are connected to a positive potential of +12 V. The positive potential is provided by regulating circuit 378, which is composed of voltage regulator 380 and a variable resistor 382 for adjusting the voltage output of voltage regulator 380. A device such as an LM317 IC chip and its associated circuitry may be used as voltage regulator 380. Positive input voltage $+V_p$ is applied to the input terminal of voltage regulator 380, and the regulated output of voltage regulator 380 is supplied to MOSFETs 314 and 316.

Similarly, MOSFETs 318 and 320 are connected to a negative potential of −12 V in this embodiment, as shown in FIG. 6C. The negative potential is provided by regulating circuit 384. Regulating circuit 384 consists of voltage regulator 386. A device such as an 79M12 IC chip and its associated circuitry may be used as the voltage regulator 386. Negative input voltage $-V_p$ is applied to an input terminal of voltage regulator 386, and the output of voltage regulator 386 is connected to the source of MOSFETs 318 and 320. The voltage applied to MOSFETs 318 and 320 is thereby kept stable.

Driver circuit 302 also includes a differential amplifying circuit 388, a resistor 392, and a peak hold circuit 394. Differential amplifying circuit 382 comprises a differential amplifier 390. An OPO7 IC chip and its associated circuitry may be used as differential amplifier 390. Resistor 392 is a 1 ohm resistor in series with the load (emitter 80) of the SOURCE− output voltage.

The differential amplifier 390 measures the current through resistor 392 and outputs a voltage signal corresponding to the current through resistor 392. Peak hold circuit 394, which may be based on an LF398 IC chip or similar circuitry, measures and holds the maximum voltage output of differential amplifier 390. The peak value of the output of differential amplifier 390 reflects the peak current generated by drive circuit 302 and may accordingly be monitored to determine whether the drive circuit 302 is functioning properly.

The pulse width watchdog circuit 306 includes comparators 400, 402, 404, and 406. RC circuits 408 and 410 are connected to the outputs of comparators 400 and 404, respectively. Comparator 400 and its associated circuitry are so designed that the output of comparator 400 is HIGH when the PHASE 1 ($\phi_1$) signal is HIGH and LOW when the PHASE 1 ($\phi_1$) signal is LOW. RC circuit 408 delays the rise of the output voltage of comparator 400 for a time interval $T_{pw}$ predetermined by the values of the resistor and capacitor in RC circuit 408. Comparator 402 compares the delayed output of comparator 400 with a reference voltage. If the delayed output of comparator 400 exceeds the reference level at the input of comparator 402, the output of comparator 402 goes LOW. Accordingly, the output of comparator 402 is HIGH unless a pulse of the PHASE 1 ($\phi_1$) signal exceeds the time interval $T_{pw}$ determined by RC circuit 408.

Comparator 404, RC circuit 410, and comparator 406 operate in essentially the same manner for the PHASE 2 ($\phi_2$) signal and will not be discussed in detail. It is sufficient to state that the output of comparator 406 is HIGH as long as the pulse of the PHASE 2 ($\phi_2$) signal does not exceed the time interval $T_{pw}$ determined by RC circuit 410.

Frequency watchdog circuit 308 includes one-shots 412 and 416 and their associated circuitry, and D-flip flops 414 and 418. One-shot 412 generates an output pulse of a predetermined length $T_f$ for each pulse of the PHASE 1 ($\phi_1$) signal. The duration of the one-shot 412 output pulse is based on the maximum allowable frequency of the PHASE 1 ($\phi_1$) and PHASE 2 ($\phi_2$) signals.

The output of one-shot 412 is sent to the D-input of D-flip flop 414, and the PHASE 1 ($\phi_1$) signal is transmitted to the clock input of D-flip flop 414. If a subsequent pulse of the PHASE 1 ($\phi_1$) signal occurs before the end of that output pulse from one-shot 412 triggered by a previous pulse of the PHASE 1 ($\phi_1$) signal, the output of D-flip flop 414 is set HIGH, thereby turning on a transistor 428 also incorporated in the frequency watchdog circuit. When transistor 428 is turned on, the ENABLE (E) signal is forced LOW; and the drive circuit 302 is turned off.

One-shot 416 and D-flip flop 418 serve the same function for the PHASE 2 ($\phi_2$) signal. Accordingly, if the frequency of either the PHASE 1 ($\phi_1$) signal or the PHASE 2 ($\phi_2$) signal exceeds the frequency determined by the length of the one-shot output pulses, the output of either D-flip flop 414 or D-flip flop 418 turns on transistor 428, thereby turning off drive circuit 302.

The power supply watchdog circuit 312 has a voltage level monitoring device 422 and associated circuitry of a conventional character. If the positive power supply voltage $+V_p$ goes below a positive threshold level $+V_{th}$ or the negative power supply voltage $-V_p$ goes above a negative threshold level $-V_{th}$, the output of the power supply monitoring device 422 is turned off. When the output of the power supply monitoring device 422 is turned off, the ENABLE (E) signal is forced LOW; and the drive circuit 302 is turned off.

The power-on reset circuit 310 consists of a timing device 420. Timing device 420 may be a 555 timer chip and its associated circuitry. If the output of comparator 402, comparator 406, transistor 428, or power supply monitoring device 422 changes from LOW to HIGH, the timing device 420 delays the change from LOW to HIGH for a time period $T_r$ (which is typically 0.5 seconds) determined by the timing device circuitry. Accordingly, all timing and drive circuits have sufficient time to become stable before the drive circuit 302 is turned back on.

A reference voltage generating circuit 430 generates a reference voltage for the comparators 400, 402, 404, and 406 of the pulse width watchdog circuit 306 and for the power supply monitoring device 422 of the power supply watchdog circuit 312.

The operation of bipolar power supply 33 will now be described with reference to FIGS. 5–10. Under normal operating conditions, the ENABLE (E) signal enables AND gates 330 and 342, allowing MOSFET driver circuits 322, 324, 326, and 328 to turn on MOSFETs 314, 316, 318, and 320, respectively, by way of the PHASE 1 ($\phi_1$) and PHASE 2 ($\phi_2$) signals. More specifically, MOSFETs 316 and 318 are turned on by the PHASE 1 ($\phi_1$) signal, and MOSFETs 314 and 320 are turned on by the inverse of the PHASE 1 ($\phi_1$) signal, $\overline{\text{PHASE 1 } \phi_1}$. The latter corresponds to the PHASE 2 ($\phi_2$) signal combined the ENABLE (E) signal using a logical AND operation. Therefore, as shown in FIGS. 7 and 8, in the time interval between $t_0$ and $t_1$, the positive source voltage signal SOURCE+ is generated while the PHASE 1 ($\phi_1$) pulses exist; and the negative source voltage SOURCE− is generated during the existence of the PHASE 2 ($\phi_2$) pulses.

MOSFET drive circuits 322, 324, 326, and 328 turn on MOSFETs 314, 316, 318, and 320, respectively, as follows. The PHASE 1 ($\phi_1$) and PHASE 2 ($\phi_2$) signals are each a series of positive pulses. In the preferred embodiment, the ENABLE (E) signal, which is also a series of positive pulses, is the PHASE 1 ($\phi_1$) and PHASE 2 ($\phi_2$) signals combined by a logical OR operation. The ENABLE (E) and PHASE 1 ($\phi_1$) signals are directly applied to the input of AND gate 342. The ENABLE (E) signal and the $\overline{\text{PHASE 1 } (\phi_1)}$, signal are applied to the input of AND gate 330. The HIGH output of AND gate 330 turns on MOSFET 314 via turn-on delay circuit 332, inverter 334, and MOSFET 336. The outputs of AND gate 330 and 342 are HIGH only when the ENABLE (E) signal pulse is HIGH. If the ENABLE (E) signal is ever LOW, the outputs of AND gates 330 and 342 are held LOW. Because MOSFETs 314 and 316 can never be switched ON when the ENABLE (E) signal is LOW, forcing the ENABLE (E) signal LOW turns off drive circuit 302.

Further, because the PHASE 1 ($\phi_1$) signal is directly connected to an input of AND gate 342 and the $\overline{\text{PHASE 1 } (\phi_1)}$ signal is connected to an input of AND gate 330, the output of AND gate 330 is HIGH only when the output of AND gate 342 is LOW, and vice versa. Thus, MOSFET drive circuits 322 and 324 never turn on MOSFETs 314 and 316 at the same time. Similarly, because MOSFET drive circuits 326 and 328 are respectively controlled by the PHASE 1 ($\phi_1$) signal and the $\overline{\text{PHASE 1 } (\phi_1)}$ signal MOSFETs 318 and 320 are theoretically never on at the same time.

In practice, however, a condition known as "shoot-through" sometimes occurs. For example, MOSFETs 314 and 318 may both momentarily be on while MOSFET 318 is turning off and MOSFET 314 is turning on. That shoot-through effectively short circuits positive voltage source $+V_p$ to negative voltage source $-V_p$ and thus must be prevented which is done by turn-on delay circuit 332 (see FIG. 9). In our example, circuit 332 allows MOSFET 314 to turn on only after a short delay period, in this embodiment 10 $\mu$sec, once the output of AND gate 330 goes HIGH.

However, turn-on delay circuit 332 does not affect the change of output of AND gate 330 from HIGH to LOW. Therefore, MOSFET 314 is turned off at the same time that the output of AND gate 330 goes from HIGH to LOW. Turn on delay circuits 344, 356, and 364 similarly delay the turning on of MOSFETs 316, 318, and 320, respectively, while allowing their corresponding MOSFETs to be turned off immediately. Accordingly, shoot-through is prevented by the turn-on delay circuits.

Referring now to FIG. 7, the interval between $t_1$ and $t_2$ is a typical one in which the pulse width watchdog circuit 306 determines that the width of a pulse of the PHASE 2 ($\phi_2$) signal occurring at time $t_1$ exceeds time period $T_{pw}$ and is therefore too wide. Accordingly, RC circuit 410 allows the output of comparator 404 to rise to a level that exceeds the reference voltage applied to comparator 406. The output of comparator 406 is therefore turned off. The ENABLE (E) signal is forced LOW by this absence of an output from comparator 406. The drive circuit 302 is switched off while the comparator 406 holds the ENABLE (E) signal LOW and until the output of comparator 406 subsequently goes HIGH.

At time $t_2$ the pulse width watchdog circuit 306 determines that the pulse width of the pulse in signal PHASE 2 ($\phi_2$) occurring immediately prior to time $t_2$ is within time period $T_{pw}$. The power-on reset circuit 310, however, keeps the ENABLE (E) signal LOW for a predetermined time period between $t_2$ and $t_3$ (0.5 $\mu$sec in this embodiment) before allowing the ENABLE (E) signal to go HIGH. Normal operation of the bipolar power supply 33 is thus resumed at time $t_3$.

FIG. 8 illustrates the situation in which the frequency watchdog circuit 308 determines that the frequency of the PHASE 1 ($\phi_1$) signal is outside a predetermined range of frequencies. Specifically, FIG. 8 represents a situation in which the frequency of the pulses of the PHASE 1 ($\phi_1$) signal exceeds a value determined by the length of the output pulse of one-shot 412. Accordingly, at time $t_1$ the output of D-flip flop 414 goes HIGH, turning on transistor 428, which forces the ENABLE (E) signal to go LOW. This turns off drive circuit 302. At time $t_2$ the frequency of the pulses of the PHASE 1 ($\phi_1$) signal again reaches an acceptable value. At this point, the power-on reset circuit holds the ENABLE (E) signal LOW for the 0.5 $\mu$sec delay period. When the delay signal expires at time $t_3$, the ENABLE (E) signal goes HIGH; and normal operation of bipolar supply 33 resumes.

FIG. 10 shows how power supply watchdog circuit 312 works. Between time $t_0$ and time $t_1$, bipolar power supply 33 operated normally. However, at time $t_1$ the positive power supply voltage $+V_p$ began to decrease toward zero. At time $t_2$, the positive power supply voltage $+V_p$ went lower than the positive threshold voltage $+V_{th}$. Accordingly, at time $t_2$ the output of the power supply monitoring device 422 went LOW, thereby forcing the ENABLE (E) signal to go LOW. The drive circuit 302 was therefore shut off at time $t_2$. Should the positive voltage source $+V_p$ at some later point in time exceed the positive threshold voltage $+V_{th}$, the power-on reset circuit 110 would allow normal or pulse outputting operation of bipolar power supply 33 to resume after the predetermined 0.5 μsec or other delay.

To drive the emissive component 102 of an infrared radiation emitter such as that identified by reference character 80 in FIGS. 3 and 4 of the drawing, bipolar power supply 33 will, as discussed above, be so operated as to output pulses with a voltage in the range of plus and minus 12 to 24 volts at a frequency in the range of 40 to 250 Hz. The width of the positive and negative pulses is preferably equal; a pair of positive and negative pulses will occupy from 5 to 20 percent of each duty cycle.

In applications of the present invention such as that described herein, it is important that the voltages of the pulses applied to the emissive element of the infrared radiation emitter, the current through the emissive layer, the width of the pulses, and the pulse frequency remain constant. Otherwise, the intensity of the infrared radiation outputted from the emitter will not remain constant; and the accuracy of the system or device in which the emitter is employed will suffer. Thus, the just-described power supply 33 with its watchdog and other monitoring circuits makes an important contribution of the accuracy of the foregoing and other devices and systems.

Referring now to FIG. 2, it will be remembered that the detector side of transducer 24 includes a detector unit 30 and a power supply 32 for supplying biasing voltage to the detector unit.

Detector unit 30 includes a boxlike housing 434 mounted on a printed circuit board 436. A monolithic, heat conductive, isothermal support 438 is installed in housing 434. This component is preferably fabricated from aluminum because of the high thermal conductivity which that element possesses.

Isothermal support 438 has a generally L-shaped configuration with two normally related, integral legs 440 and 442 separated by a transition section 444. The isothermal support is installed in detector unit housing 434 with locating and retaining lugs 446, 448, and 450 in housing 434 engaged in cooperating recesses 452, 454, and 456. These are located in the leg 440, transition section 444, and leg 442 of isothermal support 438.

Supported from and mounted in isothermal support 438 are: (a) data and reference detectors 458 and 460, (b) a beam splitter 462, and (c) the detector heaters 464 and 466 and thermistor-type current flow-limiting device 468 of a detector heater system 470. That system is employed to keep the two detectors at exactly the same, selected temperature, typically with a tolerance of not more than 0.01° C.

Detectors 458 and 460 are preferably made from lead selenide because of the sensitivity which that material possesses to electromagnetic energy having wave-lengths which are apt to be of interest Detectors of an appropriate character are disclosed in detail in patent application Ser. No. 07/528,059.

Detectors 458 and 460 are supported from heat conductive support 438 along with beam splitter 462. The beam splitter has a generally parallelepipedal configuration and is fabricated from a material such as silicon or sapphire which is essentially transparent to electromagnetic energy with wave-lengths of interest. The exposed front surface 472 of the beam splitter is completely covered with a coating (not shown) capable of reflecting to data detector 458 that infrared radiation impinging on the beam splitter which has a wavelength shorter than a selected value. Preferred is a proprietary coating supplied by Optical Coating Laboratories, Inc., Santa Rosa, California. In the illustrated exemplary embodiment of the invention, beam splitter 462 will reflect to data detector 458 as indicated by arrow 474 in FIG. 2 energy having a wavelength shorter than about 4 microns. The energy of longer wavelengths is, instead, transmitted through beam splitter 462 to reference detector 440 as is suggested by arrow 476 in the same figure Optical bandpass filters 478 and 480 are mounted in isothermal support 438 in front of data and reference detectors 458 and 460. Bandpass filters 478 and 480 are also obtained from Optical Coating Laboratories, Inc.

In the exemplary application of the present invention disclosed herein in which carbon dioxide is the gas being monitored, the data detector bandpass filter 478 is centered on a wavelength of 4.260 μm and has a bandwidth of 0.10 μm. This is two times narrower than the band passed by filter 478. The carbon dioxide absorption curve is fairly narrow and strong, and bandpass filter 478 centers the transmission band within that absorption curve. Therefore, if there is a change in carbon dioxide level in the gas(es) being analyzed, the maximum modulation for a given change in carbon dioxide level is obtained If the electromagnetic energy otherwise reached the data detector through the bandpass filter whether or not carbon dioxide was present in the gases being analyzed, the modulation of the carbon dioxide related output of data detector 458 would decrease; and accuracy would suffer.

The reference detector optical bandpass filter 480 in detector unit 30 is centered on a wavelength of 3.681 μm and has a half power bandwidth of 0.190 μm. That filter transmits maximum energy near the band absorbed by data detector 458; but there are no interfering gases that would absorb energy in the transmitted bandwidth Thus, nitrous oxide and water, the gases most apt to interfere, absorb on opposite sides of that bandwidth so the selected region is almost certain to be one where there is no absorption. This absorption of maximum energy in an adjacent bandwidth is selected so that the output from reference detector 460 will be at least as large as the output from data detector 458. This contributes markedly to the accuracy of the gas concentration indicative signal subsequently obtained by ratioing the data and reference signals.

All of that energy over the entire and same span of the infrared radiation beam reaching detector unit 30 with a wavelength shorter than the selected cutoff is reflected to data detector 458. Similarly, over the entire span of the beam, that energy with a longer wavelength is transmitted through beam splitter 462 to reference detector 460. Because of this, the physical relationship of detectors 458 and 460, and the identical dimensioning and configuration of the energy intercepting surfaces of those detectors, both detectors "see" the same image of the beam of infrared radiation. This contributes markedly to the accuracy afforded by detector unit 30.

Furthermore, the two signals to the data and reference detectors 458 and 460 are identical in time inasmuch as the detector-to-beam splitter distances are equal and the time required for the reflected and transmitted components of the beam to travel from beam splitter 462 to each of the two detectors 458 and 460 is, therefore, the same. By making the two detectors 458 and 460 spatially coincident from the optical viewpoint and coincident in time, the adverse effects on accuracy attributable to foreign material collecting on any of the optical windows 52, 54, 68, and 70 and a subsequently described window of detector unit 30 are also eliminated by the ratioing of the data and reference detector output signals.

The infrared radiation reaches beam splitter 462 through an aperture 482 in the front wall 484 of detector unit housing 434. A typically sapphire window 486 spans aperture 482 and keeps foreign material from penetrating to the interior 488 of detector unit housing 434 before the detector unit 30 is installed in transducer housing 26 and if that housing is subsequently unsealed.

To exclude extraneous energy, and thereby ensure that only the electromagnetic energy from emitter unit 28 reaches beam splitter 462, light traps 490 and 492 are provided. The first of these is a triangularly sectioned, inwardly extending, projection of monolithic, isothermal support 438. The second, cooperating light trap 494 is aligned with, fixed in any convenient fashion to, and extends inwardly from the casing-associated ledge or lip 494 of support 438 from which beam splitter 462 is supported.

The operation of transducer 24 as thus far described is believed to be apparent from the drawing and the foregoing, detailed description of the invention.

Briefly, however, electromagnetic energy in the infrared portion of the spectrum is generated by heating the source or emitter 80 of emitter unit 28, preferably by applying bipolar pulses of electrical energy across the emitter unit as discussed above. The energy thus emitted is collated and focused into a beam by the mirrored parabolic surface 206. The thus formed beam of energy exits the emitter unit 28 through the central bore 200 in base 88 and a complementary central bore 496 in cap 86 and is propagated along optical path 50 across the gas(es) flowing through airway adapter 22

Energy in a species specific band is absorbed by the gas of interest flowing through the airway adapter (typically carbon dioxide) to an extent proportional to the concentration of that gas. Thereafter, the attenuated beam passes through the aperture 482 in the front wall 484 of the detector unit casing 434, intercepted by beam splitter 462, and either reflected toward data detector 458 or transmitted to reference detector 460. The optical bandpass filters 478 and 480 in front of those detectors limit the energy reaching them to specified (and different) bands. Each of the detectors 458 and 460 therefore outputs an electrical signal proportional in magnitude to the intensity of the energy striking that detector. These signals are amplified by data detector and reference detector amplifiers (not shown) in detector unit 30 and then typically ratioed to generate a third signal accurately reflecting the concentration of the gas being monitored. The signal processor used for this purpose is independent of airway adapter 22 and transducer 24, not part of the present invention, and will accordingly not be disclosed herein.

As discussed above, the preferred lead selenide detectors 458 and 460 are extremely temperature sensitive; and it is therefore critical that these two detectors be maintained at the same temperature, preferably with the above-mentioned tolerance of not more than 0.01° C. Also, it was pointed out that this desired degree of control is readily available from the detector heating system 470 made up of data detector heater 464, reference detector heater 466, and thermistor-type, temperature-limiting control 468.

Heaters 464 and 468 in the illustrated detector unit 30 are precision, 25 ohm resistors with a tolerance of +0.5 percent. Thermistor 468 is conventional.

Referring now specifically to FIG. 2, resistance heaters 464 and 466 are installed in circularly sectioned recesses 498 and 500 extending from side-to-side in the legs 440 and 442 of monolithic, isothermal support 438, producing efficient, conductive heat transfer between the heaters and the support. Thermistor 468 is installed for the same reason in a similar, transversely extending, complementary aperture 502 in isothermal support transition section 444.

The spatial relationship between heater 464 and data detector 458 and between heater 466 and reference detector 460 are identical; and the spatial relationship between thermistor 470 and each of the heaters 464 and 466 is also identical. Furthermore, the two heaters 464 and 466 are so located with respect to the associated detectors 458 and 460 that the thermal energy emitted from the heaters travels first across the detectors and then across the current flow-limiting thermistor 468 to heat dumps provided by gaps 504 and 506. These are respectively located between: (a) the leg 440 of isothermal support 438 and the top wall 508 of detector unit housing 434, and (b) the rear wall 510 of the housing and the leg 442 of the isothermal support. The heat flow paths are identified by arrows 512 and 514 in FIG. 2. As a consequence of the foregoing and the high thermal conductivity of isothermal support 438, the data and reference detectors 458 and 460 can readily be maintained at the same temperature.

Figure 11:
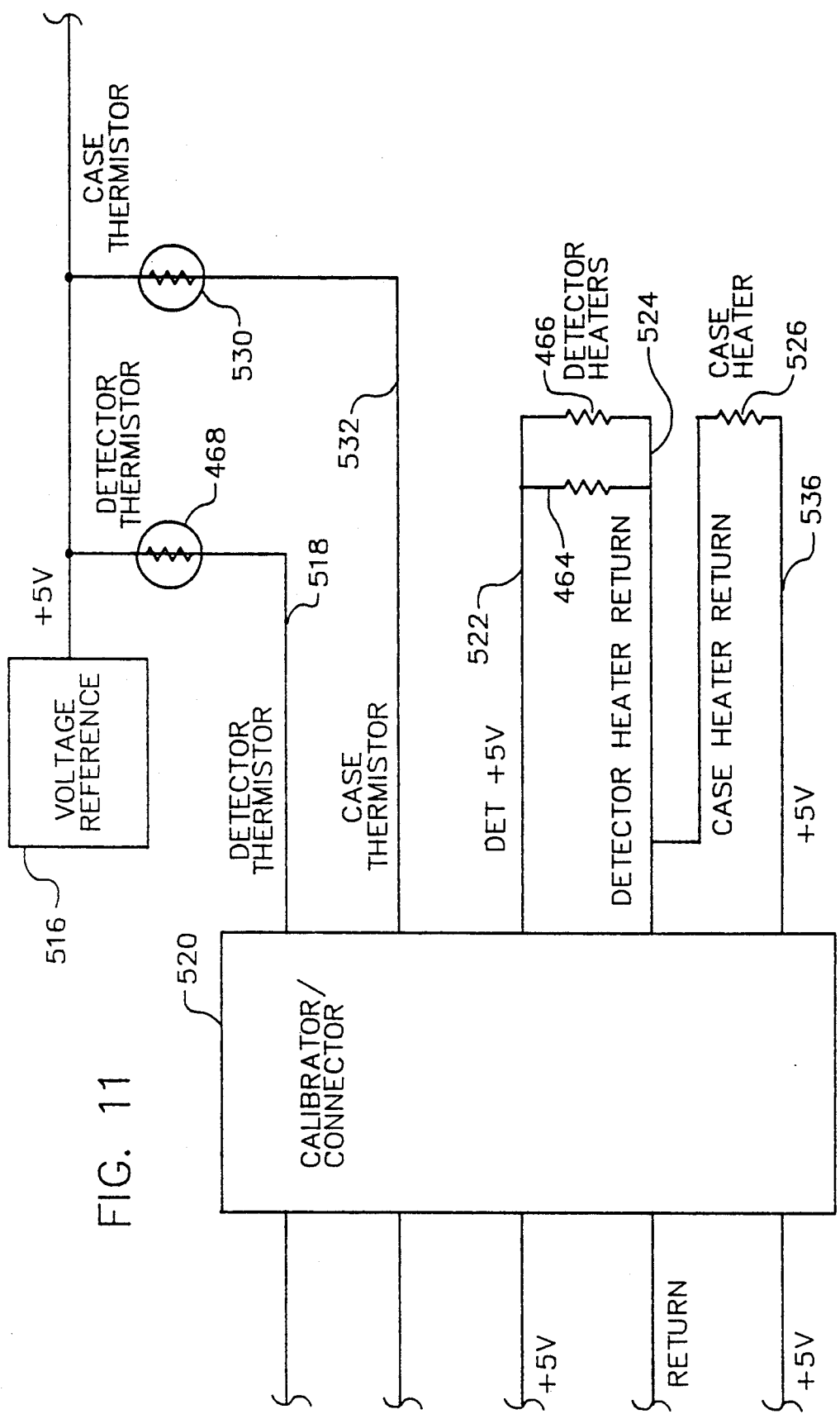
FIG. 11 is a block diagram of detector and case heating systems incorporated in the transducer.

A wiring diagram for detector heating system 70 is shown in FIG. 11. Turning then to that figure, the data detector heater 464 and reference detector heater 466 are supplied with +5 V power from a voltage reference or regulator 516 incorporated in power supply 32. This voltage is modulated by the thermistor 468 of heating system 470 to control the output from the detector heaters and maintain isothermal support 438,—and therefore data and reference detectors 458 and 460—at a constant, uniform temperature.

Detector thermistor 468 is located in an external lead 518. That lead extends from voltage regulator 516 to a calibrator/connector 520 which may be located at some distance from transducer 24. Lead 522 and heater return 524 connect the external calibrator/connector 520 to the detector heaters 464 and 466.

Unit 520, the purposes for which it is provided and the manner in which it functions are the subject of a separate application Ser. No. 600,413 filed this date. For that reason and because this unit is not part of the present invention or necessary to an understanding of the present invention, it will not be described in this specification.

It is another function of power supply 32 to supply electrical energy for biasing detectors 458 and 460. That is important because the sensitivity of those detectors to energy in the electromagnetic portion of the electromagnetic spectrum is bias dependent. Therefore, as the bias is increased, the magnitude of the signal that can be outputted for a given quantum of impinging energy is increased. However, the signals outputted from the detectors are small; and signal-to-noise ratio is accordingly a significant consideration. Twenty volts is typically the maximum bias that can be applied to the detectors without increasing the signal-associated noise to an unacceptable level.

The circuitry employed in power supply 32 for that purpose and the modus operandi of that circuitry are disclosed in parent application Ser. No. 528,059.

It will be remembered that transducer 24 also includes a data detector signal amplifier and a reference detector signal amplifier for increasing the levels of the signals outputted by data detector 458 and reference detector 460. The particular amplifiers employed for the purposes just discussed are also disclosed in parent application Ser. No. 528,509.

Transducers with detector units of the character disclosed herein are commonly used in environments in which electrical noise is prevalent. Electrostatic shielding is preferably employed to isolate the data and reference detectors and associated circuitry from the adverse effects of EMI and other radiations in the ambient surroundings. This is yet another aspect of the transducer which is disclosed in parent application Ser. No. 528,509.

Application Ser. No. 528,509 also discloses a novel casing for housing the electrostatic shielding and the detectors and other electrical and optical components of the transducer and for keeping foreign matter from reaching those components. Guide system in the casing and in the electrostatic shield facilitate the assembly of the unit and the electrical connection of the electrostatic shield to the components shielded by that device.

It was pointed out above that the just-described transducer 24 can be employed to advantage to measure the concentration of a designated gas flowing through the sampling passage 40 in airway adapter 22. As the monitoring of the gases proceeds, and with the airway adapter 22 at ambient temperature, moisture can condense out of the surrounding environment and collect on the optical windows 52 and 54 of the airway adapter and/or the windows 68, 70, and 286 of transducer 24. The result may be a degradation in performance and loss of accuracy.

This problem can be solved by maintaining the transducer housing 26 and the airway adapter 22 at an elevated temperature, preferably in the range of 42°-45° C., during the sampling process. This is accomplished with a resistance-type heater 326 mounted in the casing 26 of transducer 24 (see FIGS. 2 and 11). Resistance heater 526 keeps casing 26 and the airway adapter 22 assembled to transducer 24 at the desired temperature.

Operation of casing heater 526 is controlled by a thermistor 530 mounted on the heater and connected to calibrator/connector 520 by lead 532 (see FIG. 11).

Plus 5 V power is supplied to case heater 526 from the voltage regulator 516 in power supply 32 by way of external calibrator/connector 530 and lead 534. The opposite side of heater 526 is connected by casing heater return 536 to the return 524 from data and reference detector heaters 464 and 466.

The invention may be embodied in many specific forms in addition to those disclosed above without departing from the spirit or essential characteristics of the invention. These embodiments are therefore to be considered in all respects as illustrative and not restrictive. The scope of the invention is instead indicated by the appended claims, and all changes which come within the meaning and range of equivalency of the claims are therefore intended to be embraced therein.

What is claimed is:

1. A pulsed power supply which has:
   means comprising a positive voltage source for generating positive operating pulses and a negative voltage source for generating negative operating pulses;
   signal generating means for outputting first an output signal of one polarity and then an output signal of the opposite polarity in each duty cycle, said signal generating means having means for alternately receiving the operating pulses from the positive voltage source and the negative voltage source;
   timing means for controlling those parts of its duty cycle in which said signal generating means can output signals with first one and then the opposite polarity; and
   means for so disenabling the signal generating means as to prevent the outputting of said output signals therefrom if the operating pulses do not meet one or more specified parameters.

2. A pulsed power supply as defined in claim 1 in which the parameter is the width of the operating pulses.

3. A pulsed power supply as defined in claim 2 in which the parameter is the frequency of the operating pulses.

4. A pulsed power supply as defined in claim 1 in which the parameter is the voltage of the operating pulses.

5. A pulsed power supply as defined in claim 1 in which the parameter is exceeded by the generation of an extraneous pulse.

6. A pulsed power supply as defined in claim 1 which comprises means operable, once the signal generating means has been disenabled as aforesaid and the specified parameters have subsequently been met, to delay for a specified period the subsequent enabling of the signal generating means.

7. A pulsed power supply as defined in claim 1 in which the signal generating means comprises:
   complementary pairs of MOSFETs so arranged in an H-bridge array that one pair of MOSFETs must be turned on for said signal generating means to output a signal of said one polarity and the other pair of MOSFETs must be turned on for the signal generating means to output the signal of the opposite polarity; and
   means for preventing one of said pair of MOSFETs from being turned on while the other pair is on.

8. A pulsed power supply as defined in claim 7 which has MOSFET drive means requiring the inputting of an ENABLE signal in order to turn on one of said pairs of MOSFETs.

9. A pulsed power supply as defined in claim 8:
   wherein the parameter is the width of the operating pulses; and
   the means for disenabling the pulse generating circuit means comprises a pulse width watchdog circuit which keeps the ENABLE signal from being inputted to the MOSFET drive means for so long as the pulse width parameter is not met.

10. A pulsed power supply as defined in claim 8:
    wherein the parameter is the frequency at which operating pulses are supplied to the pulse generating circuit means; and
    the means for disenabling the pulse generating circuit means comprises a pulse frequency watchdog circuit which keeps the ENABLE signal from being inputted to the MOSFET drive means for so long as the pulse frequency parameter is not met.

11. A pulsed power supply as defined in claim 8:

wherein the parameter comprises the voltages of the operating pulses; and the means for disenabling the pulse generating circuit means comprises a power supply watchdog circuit which keeps the ENABLE signal from being inputted to the MOSFET drive means for so long as the voltage parameter is not met.

12. A pulsed power supply as defined in claim 8:

wherein the parameter is exceeded by the inputting to the MOSFET drive means of one or more extraneous pulses; and the means for disenabling the pulse generating circuit means comprises watchdog means which keeps the ENABLE signal from being inputted to the MOSFET drive means for so long as extraneous pulses are inputted to said drive means.

13. A bipolar power supply comprising:
a. control means for generating positive and negative operating pulses;
b. signal generating means electrically connected to a load for generating and applying to the load a first output signal of one polarity and a second output signal of the opposite polarity, the first and second output signals being generated based on the operating signals generated by the control means; and
c. means for monitoring the operating pulses and disenabling the signal generating means to prevent the generation of the output signals thereby if the operating pulses do not meet one or more specified parameters.

14. The bipolar power supply of claim 13, in which the parameter is at least one of: (a) the width of the operating pulses; (b) the frequency of the operating pulses; (c) the voltage of the operating pulses; and (d) the generation of an extraneous pulse.

15. The bipolar power supply of claim 13, further comprising means for delaying, once the signal generating means has been disenabled, the subsequent enabling of the signal generating means.

16. A combination of:
a. an infrared radiation emitter including an electrically resistive, emissive component; and
b. a power supply for driving said emitter comprising
   i. control means for generating positive and negative operating pulses,
   ii. signal generating means electrically connected to the emissive component for generating and applying to the emissive component a first output signal of one polarity and a second output signal of the opposite polarity, the first and second output signals being generated based on the operating signals generated by the control means, and
   iii. means for monitoring the operating pulses and disenabling the signal generating means to prevent the generation of the output signals thereby if the operating pulses do not meet one or more specified parameters.

17. The bipolar power supply of claim 16, in which the parameter is at least one of: (a) the width of the operating pulses; (b) the frequency of the operating pulses; (c) the voltage of the operating pulses; and (d) the generation of an extraneous pulse.

18. The bipolar power supply of claim 16, further comprising means for delaying, once the signal generating means has been disenabled, the subsequent enabling of the signal generating means.

* * * * *